United States Patent
Cosmescu

(10) Patent No.: US 10,595,934 B2
(45) Date of Patent: Mar. 24, 2020

(54) ELECTROSURGICAL UNIT PENCIL APPARATUS AND SHROUD HAVING DIRECTED ILLUMINATION

(75) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 1190 days.

(21) Appl. No.: 13/462,176

(22) Filed: May 2, 2012

(65) Prior Publication Data
US 2012/0283728 A1 Nov. 8, 2012

Related U.S. Application Data

(60) Provisional application No. 61/481,715, filed on May 2, 2011.

(51) Int. Cl.
| A61B 18/14 | (2006.01) |
| A61B 90/35 | (2016.01) |
| A61B 18/00 | (2006.01) |
| A61B 90/30 | (2016.01) |

(52) U.S. Cl.
CPC .......... *A61B 18/1477* (2013.01); *A61B 90/35* (2016.02); *A61B 90/30* (2016.02); *A61B 2018/00607* (2013.01); *A61B 2218/006* (2013.01)

(58) Field of Classification Search
CPC .......... A61B 19/5202; A61B 2018/006; A61B 2018/00607
USPC .......................................................... 606/2
See application file for complete search history.

(56) References Cited

U.S. PATENT DOCUMENTS

| 6,550,926 | B2 * | 4/2003 | Berger .......................... 359/882 |
| 6,562,032 | B1 * | 5/2003 | Ellman .......... A61B 17/320068 606/41 |
| 7,083,601 | B1 * | 8/2006 | Cosmescu .............. A61B 18/14 601/35 |
| 7,306,559 | B2 * | 12/2007 | Williams ................ A61B 17/02 600/245 |
| 2005/0113825 | A1 * | 5/2005 | Cosmescu .......... A61B 18/1402 606/45 |
| 2007/0049927 | A1 * | 3/2007 | Saltzman ........... A61B 18/1402 606/45 |
| 2010/0125172 | A1 * | 5/2010 | Jayaraj ..................... A61B 1/06 600/249 |

* cited by examiner

*Primary Examiner* — Joseph M Dietrich
(74) *Attorney, Agent, or Firm* — Zeman-Mullen & Ford, LLP

(57) ABSTRACT

An electrosurgery pencil having directed illumination and a removable shroud having directed illumination where the removable shroud is adapted to fit over an electrosurgery pencil.

12 Claims, 2 Drawing Sheets

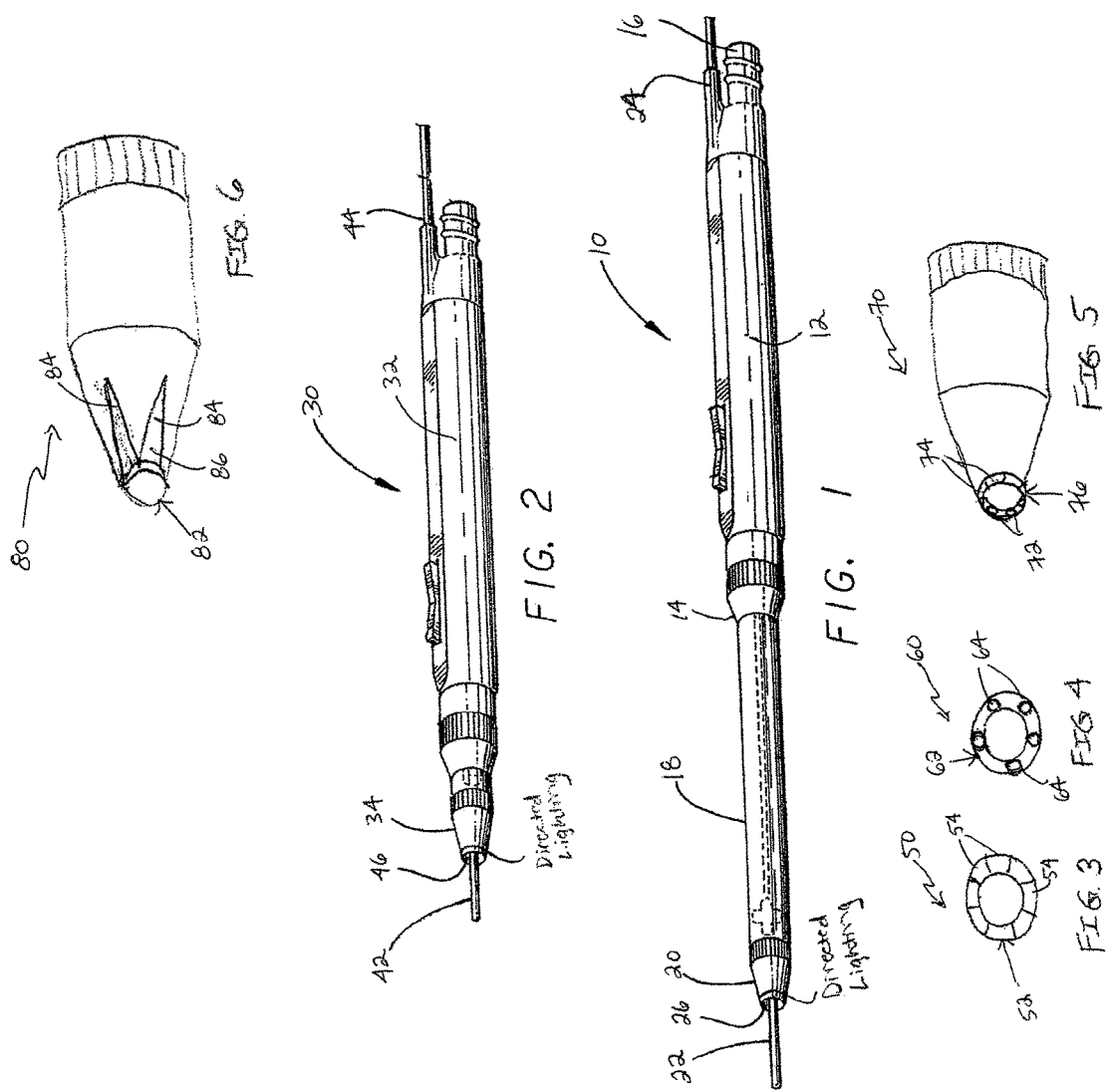

ELECTROSURGICAL UNIT PENCIL APPARATUS AND SHROUD HAVING DIRECTED ILLUMINATION

CROSS-REFERENCE TO RELATED APPLICATIONS

This application claims the benefit of, and priority to U.S. Provisional Application No. 61/481,715, filed May 2, 2011, which application is hereby incorporated by reference in its entirety.

FIELD OF INVENTION

The present invention generally relates to an electrosurgery pencil having directed illumination near the electrode contained within the electrosurgery pencil. The present invention is also directed to a removable shroud with directed illumination that is adapted to fit over an external surface of an electrosurgery pencil. More particularly, the present invention relates to an electrosurgery pencil and a removable shroud where one or both have directed illumination where the directed illumination includes at least one lighting element that is positioned around at least a portion of the circumference of the electrosurgery pencil and/or removable shroud.

BACKGROUND OF THE INVENTION

Most electrosurgery pencils now include smoke evacuation means to remove smoke, fluids, and debris away from the surgical site during a surgical procedure. However, although this removal of smoke, fluids, and debris provides a surgeon with better visibility during cutting and/or coagulation at the surgical site, some surgeries involve parts of the body that have less visibility than other parts of the body especially in those areas that are deeper in the body cavity. Further, although external lighting aids can be used that are separate and apart from the electrosurgery pencil, the use of such lighting aids is not efficient and may result in a more crowded surgical site thereby making manipulation of the electrosurgery pencil by the surgeon more difficult.

Accordingly, there is a need for an electrosurgery pencil and/or removable shroud adapted to fit over the electrosurgery pencil that can be illuminated near the end of the electrosurgery pencil or shroud where cutting and/or coagulation are taking place.

SUMMARY OF THE INVENTION

The present invention is directed to an electrosurgical unit pencil (also known as an electrosurgery pencil) with directed illumination that assists a user, such as a physician or surgeon, by lighting the area of the patient to which the physician or surgeon is applying the electrosurgery pencil. The present invention is also directed to a removable shroud with directed illumination where the removable shroud is adapted to fit over an external surface of a surgical pencil. In addition, both the electrosurgery pencil and the removable shroud may include directed illumination. The directed illumination incorporated into the electrosurgery pencil and/or the removable shroud may comprise light emitting diodes (LEDs), laser lighting, or any other lighting known in the art that is capable of being incorporated into an electrosurgery pencil and/or a removable shroud that fits over a surgical pencil. Furthermore, the electrosurgery pencil may be a telescopic electrosurgery pencil with directed illumination where the directed illumination is incorporated into the end of the telescopic electrosurgery pencil and the directed illumination is capable of being employed during the telescoping of the electrosurgery pencil and/or at any length to which the electrosurgery pencil is set after telescoping.

In one exemplary embodiment, the electrosurgery pencil of the present invention includes a handpiece having a first open end, an electrode contained within at least a portion of the handpiece wherein at least a portion of the electrode extends beyond the open first end of the handpiece, at least one electrical contact in communication with the electrode for enabling cutting and/or coagulation during a medical procedure, and at least one lighting element located near the open first end of the handpiece. The lighting element may be, but is not limited to, a light emitting diode or a laser. In addition, the lighting element may be positioned around at least a portion of the circumference of the open first end of the handpiece. The one or more lighting elements may include a plurality of lighting elements that are positioned adjacent to one another and/or spaced apart form one another to facilitate different types of illumination. In addition, the lighting elements may take several different forms including, but not limited to, rectangular shapes, circular shapes, and cone shapes. The exemplary embodiment of the electrosurgery pencil described above may include a handpiece that also has a second open end where the first and second open ends are connected by a channel and the electrosurgery pencil further includes smoke evacuation means in communication with the one or more electrical contacts for removing smoke, fluids, and debris produced during the medical procedure.

In another exemplary embodiment of the present invention, a telescopic electrosurgery pencil includes a handpiece having an open first end and an open second end connected by a channel, a telescopic tube having a first end and a second end wherein the second end of the telescopic tube is introduced into the open first end of the handpiece so that the telescopic tube is concentrically retained within the handpiece, an electrode positioned within at least a portion of the telescopic tube wherein at least a portion of the electrode extends beyond the first end of the telescopic tube, at least one electrical contact in communication with the electrode for enabling cutting and/or coagulation during a medical procedure, and at least one lighting element located near the first end of the telescopic tube. The lighting element may be, but is not limited to, a light emitting diode or a laser. In addition, the lighting element may be positioned around at least a portion of the circumference of the first end of the telescopic tube. The one or more lighting elements may include a plurality of lighting elements that are positioned adjacent to one another and/or spaced apart form one another to facilitate different types of illumination. In addition, the lighting elements may take several different forms including, but not limited to, rectangular shapes, circular shapes, and cone shapes. The exemplary embodiment of the telescopic electrosurgery pencil described above may further include smoke evacuation means in communication with the one or more electrical contacts for removing smoke, fluids, and debris produced during the medical procedure.

In yet another exemplary embodiment of the present invention, a removable shroud for use with an electrosurgery pencil includes a conduit having an open first end, an open second end, and a generally semi-circular shaped hollow interior, a handpiece holder for removably receiving an electrosurgery pencil formed continuously with at least a portion of the top outer surface of the conduit, a nozzle member positioned near the first end of the conduit where the nozzle member has a first open end through which an electrode from an electosurgery pencil can extend, and one or more lighting elements located near the open first end of the conduit and/or the first open end of the nozzle. The lighting element may be, but is not limited to, a light emitting diode or a laser. In addition, the lighting element may be positioned around at least a portion of the circumference of the first end of the open first end of the conduit and/or the first open end of the nozzle. The one or more lighting elements may include a plurality of lighting elements that are positioned adjacent to one another and/or spaced apart form one another to facilitate different types of illumination. In addition, the lighting elements may take several different forms including, but not limited to, rectangular shapes, circular shapes, and cone shapes. The exemplary embodiment of the removable shroud described above may further include smoke evacuation means connected to the open second end of the conduit for removing smoke, fluids, and debris produced during the medical procedure.

BRIEF DESCRIPTION OF THE DRAWINGS

The subject invention will hereinafter be described in conjunction with the appended drawing figures, wherein like numerals denote like elements, and FIG. 1 is a perspective view of a telescoping ESU pencil apparatus with directed illumination according to the present invention, with the telescopic electrode assembly extended;

FIG. 2 is a perspective view of the apparatus in FIG. 1 with the telescopic surgical electrode assembly retracted;

FIG. 3 is an end view of an exemplary embodiment of the directed illumination incorporated into the tip of an electrosurgery pencil where the directed illumination takes the form of a circular array of side by side LEDs that are somewhat rectangular in shape;

FIG. 4 is an end view of an exemplary embodiment of the directed illumination incorporated into the tip of an electrosurgery pencil where the directed illumination takes the form of separately positioned circular shaped LEDs that are positioned about the end circumference of the tip of the electrosurgery pencil;

FIG. 5 is a perspective view of an exemplary embodiment of the directed illumination incorporated into the tip of an electrosurgery pencil where the directed illumination takes the form of both the separately positioned circular shaped LEDs shown in FIG. 4 and LEDs incorporated side by side around an outer circumference of the tip of the electrosurgery pencil;

FIG. 6 is a perspective view of an exemplary embodiment of the directed illumination incorporated into the tip of an electrosurgery pencil where the directed illumination takes the form of cone shaped LEDs positioned about an outer circumference of the tip of the electrosurgery pencil where the larger end of the cone of light is positioned closest to the end of the electrosurgery tip.

DETAILED DESCRIPTION

Figure 7:
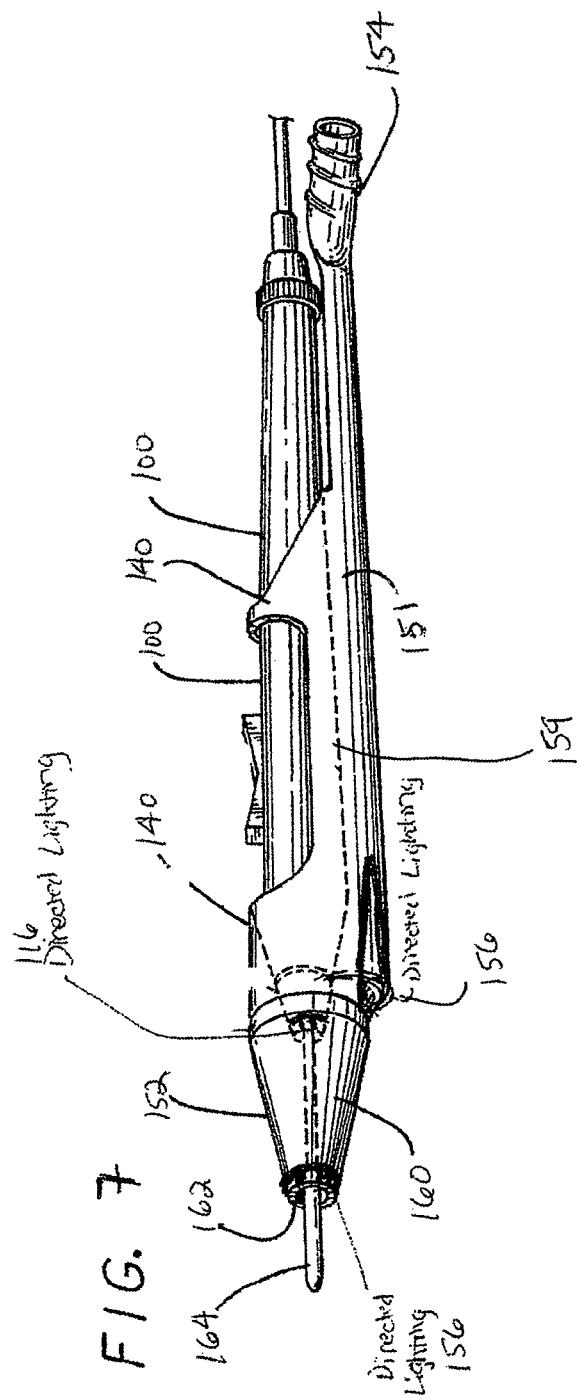
FIG. 7 is a perspective view of an ESU pencil apparatus and shroud, both with directed illumination, where the directed illumination incorporated into the ESU pencil takes the form of LEDs incorporated side by side around an outer circumference of the tip of the electrosurgery pencil and the directed illumination incorporated into the shroud takes the form of both 1) LEDs incorporated side by side around an outer circumference of the tip of the shroud and 2) one or more cone shaped LEDs positioned on an outer bottom circumference of the shroud located below the tip of the shroud.

Examples of electrosurgery pencils and shrouds adapted to fit over electrosurgery pencils in which directed illumination may be incorporated can be seen in U.S. Pat. Nos. 6,142,995 and 7,112,199, both of which are herein incorporate by reference. The directed illumination may be incorporated into one or both of the electrosurgery pencil and shroud by LEDs incorporated into the outer surfaces of the electrosurgery pencil and/or shroud or by positioning light sources currently known in the art onto the outer external surfaces of the electrosurgery pencil and/or shroud and connecting the light sources to the power source used by the electrosurgery pencil through the electrosurgery pencil contacts. Alternatively, the lighting elements or lighting sources including, but not limited to, LEDs and lasers, may be battery powered. In the embodiments where the lighting elements/sources are connected to a power source by using the electrosurgery pencil through the electrosurgery pencil electrical contacts, the lighting elements/sources can function to activate or "turn on" when the electrosurgery pencil is in use for cutting and/or coagulation and smoke evacuation and deactivate or "turn off" when the electrosurgery is not in use for cutting and/or coagulation and smoke evacuation.

A perspective view of a telescoping ESU pencil apparatus with directed illumination 10 according to the present invention, with the telescopic electrode assembly extended, is shown in FIG. 1. Telescoping ESU pencil with directed illumination 10 includes a handpiece 12 having an open first end 14 and an open second end 16 which are connected by a channel, a telescopic tube 18 having a first end 20 and a second end (not shown) where the second end of the telescopic tube 18 is introduced into the open first end 14 of handpiece 12 so that the telescopic tube 18 is concentrically retained within the handpiece 12, an electrode 22 positioned within at least a portion of the telescopic tube 18 where at least a portion of the electrode 22 extends beyond the first end 20 of the telescopic tube, at least one electrical contact 24 in communication with the electrode 22 for enabling cutting and/or coagulation during a medical procedure, and at least one lighting element 26 located near the first end 20 of the telescopic tube 18.

FIG. 2 is a perspective view of the apparatus in FIG. 1 with the telescopic surgical electrode assembly retracted thereby depicting what a non-telescoping electrosurgery pencil with directed illumination may look like. Electrosurgery pencil with directed illumination 30 includes a handpiece 32 having an open first end 34, an electrode 42 contained within at least a portion of the handpiece 32 where at least a portion of the electrode 42 extends beyond the open first end 34 of the handpiece 32, at least one electrical contact 44 in communication with the electrode for enabling cutting and/or coagulation during a medical procedure, and at least one lighting element 46 located near the open first end 34 of the handpiece 32.

An end view of an exemplary embodiment of the directed illumination 50 incorporated into the tip of an electrosurgery pencil where the directed illumination 50 takes the form of a circular array 52 of side by side LEDs 54 that are somewhat rectangular in shape is shown in FIG. 3. An end view of an exemplary embodiment of the directed illumination 60 incorporated into the tip of an electrosurgery pencil where the directed illumination 60 takes the form of separately positioned circular shaped LEDs 64 that are positioned about the end circumference 62 of the tip of the electrosurgery pencil is shown in FIG. 4.

FIG. 5 is a perspective view of an exemplary embodiment of the directed illumination 70 incorporated into the tip of an electrosurgery pencil where the directed illumination 70 takes the form of both the separately positioned circular shaped LEDs 72 shown in FIG. 4 and LEDs 74 incorporated side by side (shown in FIG. 3) around an outer circumference 76 of the tip of the electrosurgery pencil. FIG. 6 is a perspective view of an exemplary embodiment of the directed illumination 80 incorporated into the tip of an electrosurgery pencil where the directed illumination 80 takes the form of cone shaped LEDs 84 positioned about an outer circumference 82 of the tip of the electrosurgery pencil where the larger end of the cone of light 86 is positioned closest to the end of the electrosurgery tip.

FIG. 7 is a perspective view of an ESU pencil apparatus 100 and shroud 140, both with directed illumination 116, 156. The removable shroud 140 with directed illumination 156 includes a conduit 151 having an open first end 152, an open second end 154, and a generally semi-circular shaped hollow interior, a handpiece holder 159 for removably receiving the electrosurgery pencil 100 formed continuously with at least a portion of a top outer surface of the conduit 151, a nozzle member 160 positioned near the first end 152 of the conduit 151 where the nozzle member 160 has a first open end 162 through which an electrode 164 from electrosurgery pencil 100 can extend, and at least one lighting element 156, 116 located near the open first end 152 of the conduit 151 and/or the first open end 162 of the nozzle 160.

The directed illumination may be incorporated into the electrosurgery pencil in any number of ways and may comprise any number of configurations. For example, LEDs may be incorporated into the tip of the electrosurgery pencil as shown in FIGS. 3 and 4 where the LEDs project from the end of the tip of the pencil. In FIG. 3, the LEDs take the form of a circular array of side by side LEDs. In FIG. 4, the LEDs take the form of separately positioned LEDs that are positioned about the end circumference of the tip of the electrosurgery pencil. FIG. 5 shows LEDs incorporated side by side around an outer circumference of the tip of the electrosurgery pencil as well as LEDs positioned separately about the end circumference of the tip of the electrosurgery device (like those shown in FIG. 4). It will be understood by those skilled in the art that any one or more configurations of lighting (using LEDs, laser lighting, etc) may be incorporated into the electrosurgery pencil and/or a removable shroud that fits around the electrosurgery pencil. The electrosurgery pencil incorporating directed illumination may or may not be telescoping and may or may not have a channel located therein for evacuating smoke from the surgical site.

FIG. 6 shows still another exemplary embodiment of an electrosurgery pencil tip having directed illumination where LEDs are positioned about the outer circumference of the tip in a cone shape with the larger end of the cone of light positioned closest to the end of the electrosurgery tip. FIG. 7 shows a number of different directed illumination configurations incorporated into both the tip of the electrosurgery pencil and the shroud (both the outer circumference of the tip of the shroud and the outer circumference of the bottom of the shroud).

The detailed description of exemplary embodiments of the invention herein shows various exemplary embodiments and the best modes, known to the inventor at this time, of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included figures are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

The invention claimed is:

1. An electrosurgery pencil comprising:
   a handpiece having an open first end;
   an electrode contained within at least a portion of the handpiece wherein at least a portion of the electrode extends beyond the open first end of the handpiece;
   at least one electrical contact in communication with said electrode for enabling at least one of cutting and coagulation during a medical procedure; and
   at least one lighting element located near the open first end of the handpiece wherein said at least one lighting element is connected to said at least one electrical contact so that said at least one lighting element turns on when the electrode is being used for at least one of cutting and coagulation and turns off when said electrode is not in use.

2. The electrosurgery pencil of claim 1 wherein said at least one lighting element comprises at least one of a light emitting diode and a laser.

3. The electrosurgery pencil of claim 1 wherein said at least one lighting element is positioned around at least a portion of a circumference of the open first end of the handpiece.

4. The electrosurgery pencil of claim 3 wherein said at least one lighting element comprises a plurality of lighting elements positioned adjacent to one another and/or spaced apart from one another.

5. The electrosurgery pencil of claim 4 wherein said plurality of lighting elements comprise at least one of a rectangular shape, a circular shape, and a cone shape.

6. The electrosurgery pencil of claim 1 wherein the handpiece further comprises an open second end wherein the open first end and open second end are connected by a channel and the electrosurgery pencil further comprises smoke evacuation means in communication with said at least one electrical contact for removing at least one of smoke, fluids, and debris produced during said medical procedure.

7. A telescopic electrosurgery pencil comprising:
   a handpiece having an open first end and an open second end connected by a channel;
   a telescopic tube having a first end and a second end wherein said second end of the telescopic tube is introduced into the open first end of the handpiece such that the telescopic tube is concentrically retained within the handpiece;
   an electrode positioned within at least a portion of the telescopic tube wherein at least a portion of the electrode extends beyond the first end of the telescopic tube;

at least one electrical contact in communication with said electrode for enabling at least one of cutting and coagulation during a medical procedure; and at least one lighting element located near the first end of the telescopic tube wherein said at least one lighting element is connected to said at least one electrical contact so that said at least one lighting element turns on when the electrode is being used for at least one of cutting and coagulation and turns off when said electrode is not in use.

8. The telescopic electrosurgery pencil of claim 7 wherein said at least one lighting element comprises at least one of a light emitting diode and a laser.

9. The telescopic electrosurgery pencil of claim 7 wherein said at least one lighting element is positioned around at least a portion of a circumference of the first end of the telescopic tube.

10. The telescopic electrosurgery pencil of claim 9 wherein said at least one lighting element comprises a plurality of lighting elements positioned adjacent to one another and/or spaced apart from one another.

11. The telescopic electrosurgery pencil of claim 10 wherein said plurality of lighting elements comprise at least one of a rectangular shape, a circular shape, and a cone shape.

12. The telescopic electrosurgery pencil of claim 7 further comprising smoke evacuation means in communication with said at least one electrical contact for removing at least one of smoke, fluids, and debris produced during said medical procedure.

* * * * *